United States Patent
Trsar et al.

(10) Patent No.: US 7,209,860 B2
(45) Date of Patent: Apr. 24, 2007

(54) DISTRIBUTED EXPERT DIAGNOSTIC SERVICE AND SYSTEM

(75) Inventors: Dale A. Trsar, Mt. Prospect, IL (US); Tyrone J. Moritz, Morton Grove, IL (US); Mark H. Petersen, Mundelein, IL (US); Edward A. Maron, Woodstock, IL (US); Richard H. Shepherd, McHenry, IL (US); Randall S. Harbin, Crystal Lake, IL (US); Neil Davis, Stockton, CA (US); Mary Beth Siddons, McHenry, IL (US); David R. Ellingen, Escondido, CA (US); Brad R. Lewis, Gilroy, CA (US)

(73) Assignee: Snap-On Incorporated, Kenosha, WI (US)

( * ) Notice: Subject to any disclaimer, the term of this patent is extended or adjusted under 35 U.S.C. 154(b) by 114 days.

(21) Appl. No.: 10/613,230

(22) Filed: Jul. 7, 2003

(65) Prior Publication Data

US 2005/0021294 A1    Jan. 27, 2005

(51) Int. Cl.
*G06F 15/00* (2006.01)
(52) U.S. Cl. .................. 702/183; 701/29
(58) Field of Classification Search ........... 702/19, 702/32, 113–115, 182–185, 187, 188; 701/29, 701/33; 700/26; 707/6; 705/3; 600/300, 600/508
See application file for complete search history.

(56) References Cited

U.S. PATENT DOCUMENTS

| 5,107,500 | A | * | 4/1992 | Wakamoto et al. ........... 714/26 |
|---|---|---|---|---|
| 5,566,092 | A | * | 10/1996 | Wang et al. ................ 702/185 |
| 5,631,831 | A | * | 5/1997 | Bird et al. ................... 701/29 |
| 5,660,183 | A | * | 8/1997 | Chiang et al. .............. 600/508 |
| 5,905,868 | A | * | 5/1999 | Baghai et al. .............. 709/224 |
| 6,041,182 | A | * | 3/2000 | Hart et al. .................... 706/50 |
| 6,075,438 | A | * | 6/2000 | Abe et al. .............. 340/286.01 |
| 6,141,608 | A | | 10/2000 | Rother |
| 6,584,432 | B1 | * | 6/2003 | Holzinger et al. .......... 702/188 |
| 6,584,445 | B2 | * | 6/2003 | Papageorge .................... 705/3 |
| 6,609,217 | B1 | * | 8/2003 | Bonissone et al. ............ 714/26 |
| 6,633,782 | B1 | * | 10/2003 | Schleiss et al. ............... 700/26 |
| 6,656,125 | B2 | * | 12/2003 | Misczynski et al. ........ 600/508 |
| 6,691,023 | B2 | * | 2/2004 | Fujino et al. ............... 701/114 |
| 6,754,655 | B1 | * | 6/2004 | Segal ............................ 707/6 |
| 6,820,049 | B1 | * | 11/2004 | Monroe et al. ............... 703/21 |
| 2001/0025371 | A1 | * | 9/2001 | Sato et al. ...................... 717/4 |
| 2002/0007237 | A1 | * | 1/2002 | Phung et al. .................. 701/33 |
| 2002/0107641 | A1 | * | 8/2002 | Schaeffer et al. ............. 702/19 |
| 2003/0177417 | A1 | * | 9/2003 | Malhotra et al. ............. 714/42 |
| 2004/0243532 | A1 | * | 12/2004 | Steward ....................... 706/57 |

* cited by examiner

*Primary Examiner*—Marc S. Hoff
*Assistant Examiner*—Mohamed Charioui
(74) *Attorney, Agent, or Firm*—McDermott Will & Emery LLP

(57) ABSTRACT

An expert diagnostic service system using a distributed architecture for generating expert diagnostic suggestions based on input received from a plurality of diagnostic systems. The expert service system collects data related to effective diagnostic results, such as effective fixes, corresponding to various symptoms/faults from a plurality of diagnostic systems via a data transmission network, and accumulates the number of each effective fix corresponding to each of the various symptoms. The expert service system then assigns at least one effective fix to one of the various symptoms based on a result of the accumulating step, such as the rank of the accumulated number of each fix. The expert service system uses the assigned fix corresponding to a symptom as expert suggestions.

22 Claims, 6 Drawing Sheets

FIG. 2

1993 PONTIAC BONNEVILLE 3.8 1

VEHICLE IDENTIFICATION | TEST ANALYSIS

SYMPTOMS

| SYMPTOM | CAUSE | TEST PROCEEDURE | RANK |
|---|---|---|---|
| BATTERY GOES DEAD | ACCESS VEHICLE FAULT CODES | FAULT CODE RETRIEVAL | 10 |
| NO START, NO OR SLOW CRANK | LEAKING SUPCHGR INTAKE GAS | QUICK TIP | 8 |
| NO START, CRANKS OR | INJECTOR DRIVER/INJ FLOW | FUEL INJECTOR-MFI | 7 |
| HARD START, SLOW CRANK | VACUUM LEAK | VACUUM LEAK | 5 |
| HARD START, CRANKS OK | DEFECTIVE PCM BOARD | QUICK TIP | 4 |
| ENG STARTS AND DIES | EGR SYSTEM | EGR | 4 |
| ENG DIES AT IDLE/DECEL/BRKG | IAC CIRCUIT | IDLE AIR CONTROL SOLENOID | 4 |
| ENG DIES AT ACCEL/CRUISE | IGNITION SYSTEM | ENGINE RUNNING-DIS AND MFI | 4 |
| HESITATION/STUMBLD/SAG | MAF CIRCUIT | MASS AIR FLOW SENSOR | 4 |
| MISFIRE | GROUNDED OR BROKEN MOUNT | QUICK TIP | 3 |
| RUNS ROUGH | THROTTLE BORE COKING | QUICK TIP | 3 |
| IDLE SPEED LOW | TP CIRCUIT | THROTTLE POSITION SENSOR | 3 |
| IDLE SPEED HIGH | INCORRECT FUEL PRESS/VOLUME | FUEL DELIVERY-MFI | 2 |
| IDLE SPEED HUNTING | POOR FUEL QUALITY | QUICK TIP | 2 |
| LACK OF POWER/SLUGGISH | TCC WILL NOT DISENGAGE | QUICK TIP | 2 |
| SURGES/CHUGGLES | COMPRESSOR/VALVE TIMING | ENGINE MECHANICAL - DIS | 1 |
| POOR FUEL ECONOMY | | | |
| EXHAUST ODOR/BLACK SMOKE | | | |
| BACKFIRE THRU INTAKE/EXH | | | |

DISTRIBUTED EXPERT DIAGNOSTIC SERVICE AND SYSTEM

FIELD OF THE DISCLOSURE

The present disclosure generally relates to methods and systems for providing expert suggestions on diagnostics, and more specifically, to an expert diagnostic service and system that use distributed architecture to collect effective fixes for various symptoms from a plurality of sources, and based on the collected fixes, generate recommendations to diagnose various devices/systems, such as vehicles, computers, electronic devices, electrical equipment, machines, engines, etc.

BACKGROUND OF THE DISCLOSURE

Various types of expert diagnostic systems provide standard test sequences and/or suggestions on diagnosing machines or patients. For example, a medical expert system solicits input related to a patient's symptoms and provides assistance on finding causes of the symptoms and cures thereof. Some expert diagnostic systems provide expert suggestions on what types of tests should be conducted to isolate sources of problems, and what types of fixes are available for such problems. These expert suggestions are created by a group of experienced experts or technicians, and implemented as software or control codes to be executed by the diagnostic systems.

Such type of expert diagnostic systems has its limitations and drawbacks. For a new model of machine or vehicle, it usually takes months or years for problems to develop, and for experts to become familiar with the machines or vehicles, and their problems. Thus, it usually takes a long time before an expert diagnostic system can be developed for a specific model of machine or vehicle.

In addition, the effectiveness of an expert diagnostic system is limited to the source of experts who created the system. For example, if an expert diagnostic system is created in Arizona, the experts are likely to be from that geographic area and thus problems they have encountered tend to be homogeneous. Thus, although an expert diagnostic system created by such experts may work well to solve problems for machines or vehicles in areas having weather conditions similar to those of Arizona, the conventional expert diagnostic system may not have sufficient expertise to solve problems for machines operated under different weather conditions, such as Alaska.

Moreover, the wisdom of conventional expert diagnostic systems is also limited to the small number of experts who created the expert diagnostic systems. Given the limited number of experts participated in the development of conventional expert diagnostic systems, it is unlikely that a conventional expert diagnostic system would be sufficiently sophisticated to address different types of problems effectively. Furthermore, after an expert diagnostic system is available, it usually takes a long time to develop updates for the systems and distribute the same to consumers.

Therefore, there is a need to design an expert diagnostic system with wisdom from as many experts as possible. There is another need to have an expert diagnostic system designed by experts having diverse backgrounds in order to address as many-types of problems as possible. There is also a need to provide expert suggestions for new models of machines or vehicles as soon as possible. An additional need exists to automate the process for collecting wisdom from different experts and to implement such wisdom into the expert diagnostic system dynamically.

SUMMARY OF THE DISCLOSURE

An exemplary expert service system addresses the above-noted needs as well as other needs. The exemplary expert service system dynamically obtains data related to effective fixes corresponding to various symptoms or faults from a plurality of diagnostic systems via a data transmission network. The expert service system then categorizes and validates the collected data, and generates information related effective fixes corresponding to each fault or symptom based on the collected data. The expert service system then provides expert suggestions related to effective fixes to each problem to the plurality of diagnostic systems. The expert service system may be implemented as a server that allows diagnostic systems to connect to, and establish communication with, the server via a data transmission network, such as the internet.

In one aspect, the expert service system performs additional analysis on the data received from the diagnostic systems to provide a prediction of possible failure of a specific part and/or component for a specific model year of vehicle. For each vehicle of a specific model year, the expert service system may use statistical methods, such as regression analysis, to determine what components may experience problem after a certain mileage range or period of time based on the data received from the diagnostic systems. The prediction is included in the expert suggestions. Once the diagnostic system receives such data, the diagnostic system may generate a report to vehicle owners regarding possible failures of various components so that preventative measure can be taken to prevent unexpected breakdown. The diagnostic systems may link the data related to expert suggestions to a client database that includes data related to client's vehicles and personal information, such as name, telephone number and address. When the client's vehicle fits the prediction scenario, such as after certain mileage, the diagnostic system may prompt technicians to notify the vehicle owner for a check.

In another aspect, the expert service system allows only authorized diagnostic systems to access the expert suggestions. The authorized diagnostic systems may include diagnostic systems that have subscribed to the service or have sent data related to fixes corresponding to symptoms to the expert service system, etc. The diagnostic systems may include systems for diagnosing machines, vehicles, electronic devices, patients, and the like.

Additional aspects and advantages of the present disclosure will become readily apparent to those skilled in this art from the following detailed description, wherein only exemplary embodiments of the present disclosure is shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawings and in which like reference numerals refer to similar elements and in which:

FIG. 2 shows a snapshot of an exemplary user interface of the diagnostic system.

DETAILED DESCRIPTION OF THE DISCLOSURE

In the following description, for the purposes of explanation, numerous specific details are set forth in order to provide a thorough understanding of the present disclosure. It will be apparent, however, to one skilled in the art that the present disclosure may be practiced without these specific details. In other instances, well-known structures and devices are shown in block diagram form in order to avoid unnecessarily obscuring the present disclosure.

System Architecture

Figure 1A:
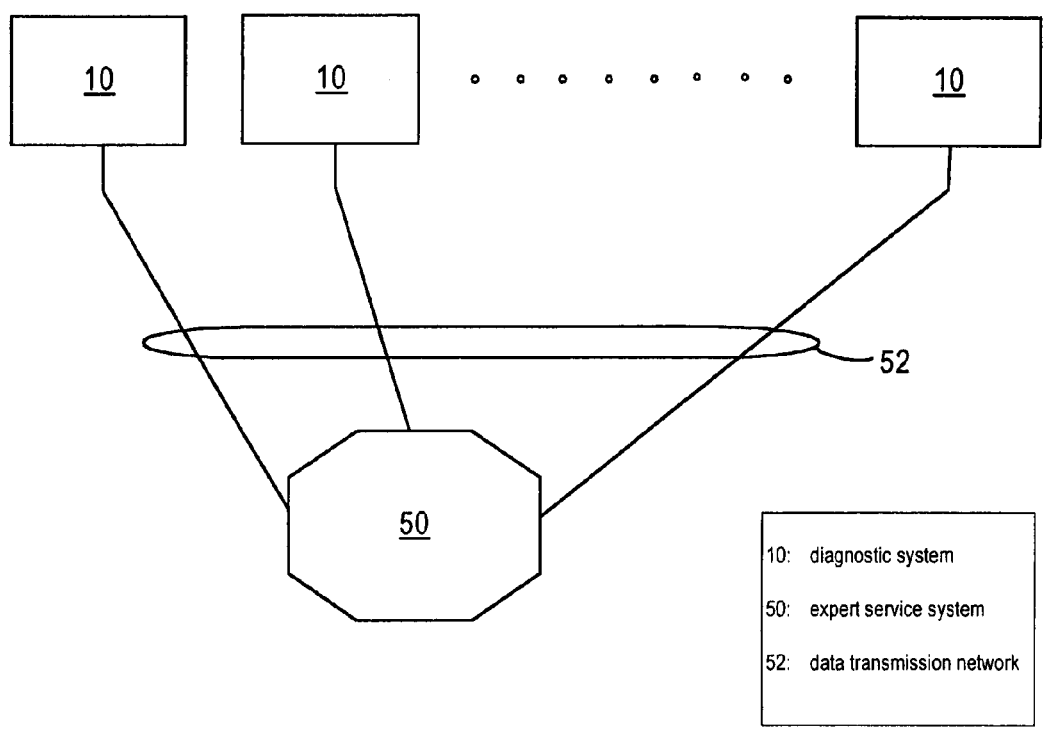
FIG. 1A is a block diagram showing system architecture of an exemplary expert service system.

FIG. 1A is a block diagram showing system architecture of an exemplary expert diagnostic system according this disclosure for providing diagnostic suggestions to assist diagnosing vehicles. Referring to FIG. 1A, a plurality of diagnostic systems 10 are connected to, and in communication with, an expert service system 50 via a data transmission network 52. Each of the diagnostic systems 10 may be of any type, such as engine analyzers, battery testers, aligner, balancer, computer testers, equipment testers, medical diagnostic systems, etc. The expert service system 50 may be implemented in a data processing system, such as a server.

Figure 1B:
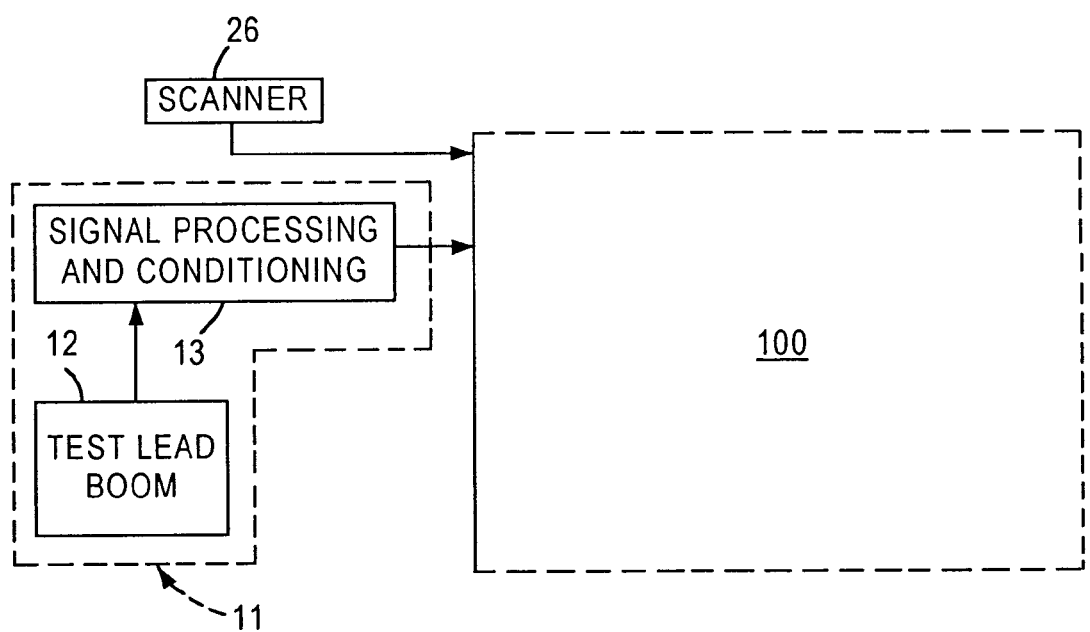
FIG. 1B shows an exemplary diagnostic system implemented as an engine analyzer.

FIG. 1B shows an exemplary diagnostic system 10 implemented as an engine analyzer. The diagnostic system 10 includes a data processing system 100 and associated equipment/circuits connected to the data processing system 100, such as engine analyzer circuit 11 and scanner 26. The engine analyzer circuit 11 is typically equipped with a test lead boom 12, including a plurality of test leads and/or sensors adapted to be connected to various points of a vehicle engine, and a signal processing and conditioning circuit 13 for interfacing the test lead boom to the data processing system 100. The scanner 26 is implemented for connecting to an on-board computer to retrieve data stored therein. The data obtained by the scanner is passed to the data processing system 100 for further processing. Detailed structures and operations of the diagnostic systems are also described in U.S. Pat. No. 6,615,120, titled "SYSTEM FOR DYNAMIC DIAGNOSIS OF APPARATUS OPERATING CONDITIONS," issued on Sep. 02, 2003, U.S. provisional application No. 60/063,361, filed Oct. 28, 1997, and U.S. Pat. No. 6,141,608, all assigned to the assignee of the current application, the entireties of which are incorporated herein by reference.

Figure 1C:
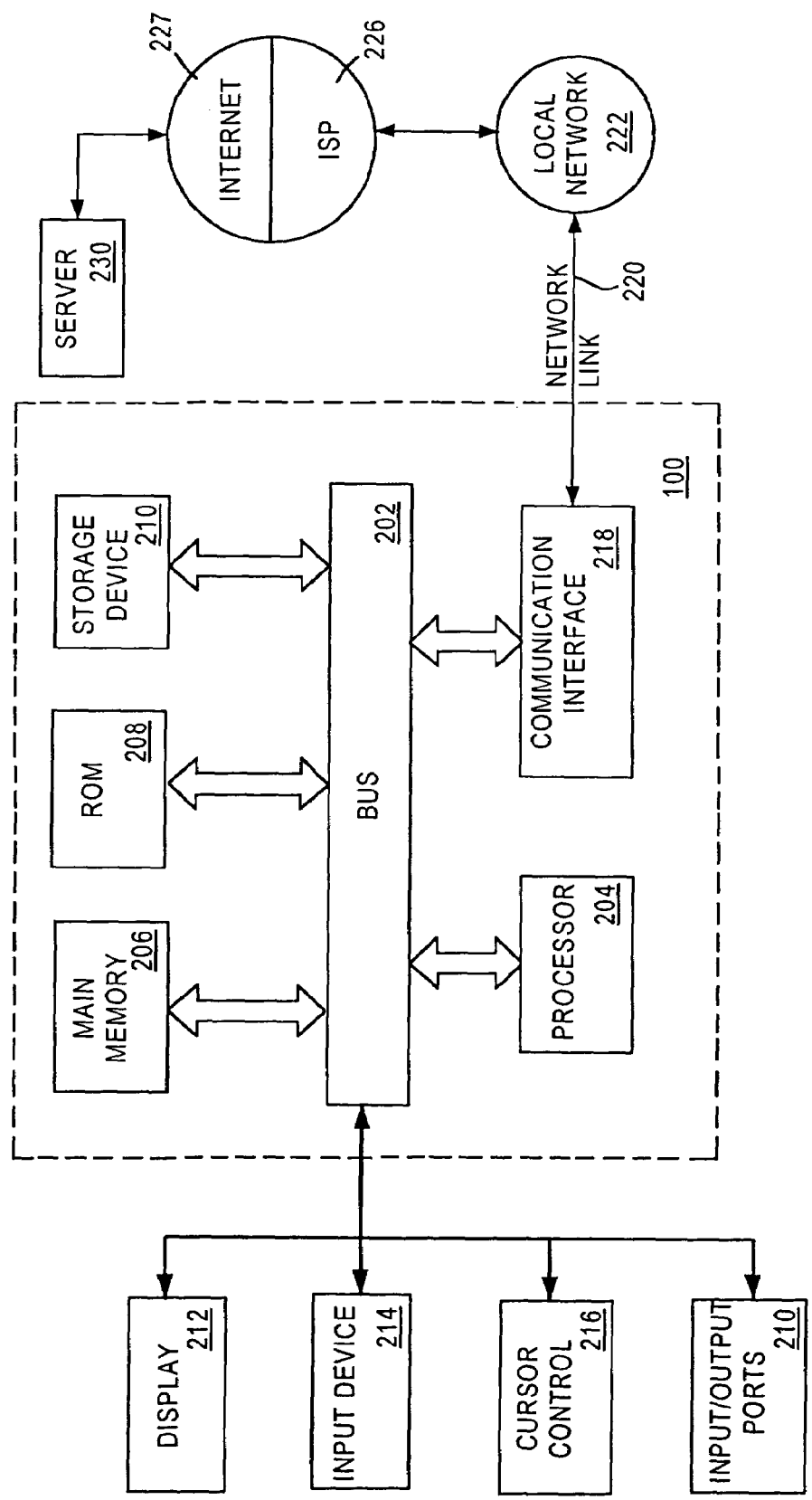
FIG. 1C depicts a block diagram of an exemplary data processing system that can be used to implement the diagnostic system and the expert service system according to this disclosure.

FIG. 1C shows a block diagram of an exemplary data processing system upon which a diagnostic system 10 and/or an expert service system 50 may be implemented. The data processing system 100 includes a bus 202 or other communication mechanism for communicating information, and a data processor 204 coupled with bus 202 for processing data. Data processing system 100 also includes a main memory 206, such as a random access memory (RAM) or other dynamic storage device, coupled to bus 202 for storing information and instructions to be executed by processor 204. Main memory 206 also may be used for storing temporary variables or other intermediate information during execution of instructions to be executed by data processor 204. Data processing system 100 further includes a read only memory (ROM) 208 or other static storage device coupled to bus 202 for storing static information and instructions for processor 204. A storage device 210, such as a magnetic disk or optical disk, is provided and coupled to bus 802 for storing information and instructions.

The data processing system 100 may be coupled via bus 202 to a display 212, such as a cathode ray tube (CRT) or liquid crystal display (LCD), for displaying information to an operator. An input device 214, including alphanumeric and other keys, is coupled to bus 202 for communicating information and command selections to processor 204. Another type of user input device is cursor control 216, such as a mouse, a trackball, or cursor direction keys and the like for communicating direction information and command selections to processor 204 and for controlling cursor movement on display 212.

The data processing system 100 is controlled in response to processor 204 executing one or more sequences of one or more instructions contained in main memory 206. Such instructions may be read into main memory 206 from another machine-readable medium, such as storage device 210. Execution of the sequences of instructions contained in main memory 206 causes processor 204 to perform the process steps described herein. In alternative embodiments, hard-wired circuitry may be used in place of or in combination with software instructions to implement the disclosure. Thus, embodiments of the disclosure are not limited to any specific combination of hardware circuitry and software.

The term "machine readable medium" as used herein refers to any medium that participates in providing instructions to processor 204 for execution. Such a medium may take many forms, including but not limited to, non-volatile media, volatile media, and transmission media. Non-volatile media includes, for example, optical or magnetic disks, such as storage device 210. Volatile media includes dynamic memory, such as main memory 206. Transmission media includes coaxial cables, copper wire and fiber optics, including the wires that comprise bus 202. Transmission media can also take the form of acoustic or light waves, such as those generated during radio wave and infrared data communications.

Common forms of machine readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a data processing system can read.

Various forms of machine-readable media may be involved in carrying one or more sequences of one or more instructions to processor 204 for execution. For example, the instructions may initially be carried on a magnetic disk of a remote data processing system, such as a server. The remote data processing system can load the instructions into its dynamic memory and send the instructions over a telephone line using a modem. A modem local to data processing system 100 can receive the data on the telephone line and use an infrared transmitter to convert the data to an infrared signal. An infrared detector can receive the data carried in the infrared signal and appropriate circuitry can place the data on bus 202. Bus 202 carries the data to main memory 206, from which processor 204 retrieves and executes the instructions. The instructions received by main memory 206 may optionally be stored on storage device 210 either before or after execution by processor 204.

Data processing system 100 also includes a communication interface 218 coupled to bus 202. Communication interface 218 provides a two-way data communication coupling to a network link 220 that is connected to a local network 222. For example, communication interface 218 may be an integrated services digital network (ISDN) card or a modem to provide a data communication connection to a corresponding type of telephone line. As another example, communication interface 218 may be a local area network (LAN) card to provide a data communication connection to a compatible LAN. Wireless links may also be implemented. In any such implementation, communication interface 218 sends and receives electrical, electromagnetic or optical signals that carry digital data streams representing various types of information. The data processing system 100, when implemented in the diagnostic system 10, may connect to a data processing system implemented in the expert service system 50 via the communication interface 218.

Network link 220 typically provides data communication through one or more networks to other data devices. For example, network link 220 may provide a connection through local network 222 to data equipment operated by an Internet Service Provider (ISP) 226. ISP 226 in turn provides data communication services through the world large packet data communication network now commonly referred to as the Internet 227. Local network 222 and Internet 227 both use electrical, electromagnetic or optical signals that carry digital data streams. The signals through the various networks and the signals on network link 220 and through communication interface 218, which carry the digital data to and from data processing system 100, are exemplary forms of carrier waves transporting the information.

Data processing system 100 can send messages and receive data, including program code, through the network(s), network link 220 and communication interface 218. In the Internet example, a server 230 might transmit a requested code for an application program through Internet 227, ISP 226, local network 222 and communication interface 218.

The data processing system 100 also has various signal input/output ports 210 for connecting to and communicating with peripheral devices and/or the scanner 26, the analyzer circuit 11, and/or other test circuits, connectors, cables, leads, probes, etc. The input/output ports 210 may include USB port, PS/2 port, serial port, parallel port, IEEE-1394 port, infra red communication port, etc., and/or other proprietary ports. The data processing system 100 may communicate with other data processing systems via such signal input/output ports 210. As shown in FIG. 1B, interfacing equipment/circuits and/or testing equipment may connect to the data processing system 100 via the input/output ports 210.

System Operation

The diagnostic system 10 provides a fault-based diagnosis of a vehicle, in which the system presents a menu of faults or symptoms indicated, e.g., by symptoms or service codes. A user selects one or more of the listed symptoms or faults that are pertinent to the vehicle under diagnosis. Based on the selected faults or symptoms, the system 10 presents a list of suggested tests or fixes to be performed to diagnose or cure the faults or symptoms. The tests or fixes are listed in the order in which they would most likely be effective in diagnosing the vehicle faults.

FIG 2 shows a snapshot of an exemplary user interface of the diagnostic system 10. The user interface has a series of icons designated "Vehicle Identification" and "Test/Analysis." When the Vehicle Identification icon is selected, the diagnostic system 10 presents the user with a number of questions or fields, such as model year, make, model name, engine size and the like, each field presenting the user with a menu of unique values from within that field from which the user may select to identify the vehicle under diagnosis.

Once the vehicle is identified, the user is able to begin diagnosis by selecting the Test/Analysis icon 32, the diagnostic system 10 brings up a screen display 39 as shown in FIG 2. A list of symptoms 40 related to the vehicle under diagnosis is displayed in the foreground in the screen display 39. The list of symptoms 40 presented to the user is representative of industry symptom diagnosis and supports the majority of drivability complaints.

A standard list of symptoms is possible because vehicles use common technology. They each have mechanical, ignition, fuel, and computer components that function in roughly the same manner. Other more specific symptoms can usually be assigned to one or more of the symptoms from the main symptom list. For example, a specific symptom of "Vehicle Dies When Taking a Right Turn" will fit under a less specific symptom of "Vehicle Dies at Idle/Deceleration/Braking." The tests to diagnose the condition are generally the same. A standard list of symptoms is used because it provides a consistent interface and diagnostic philosophy for all vehicles.

When a user selects one or more of the listed symptoms which are exhibited by the vehicle under test, the screen display 39 presents a list 42 of possible causes of the symptom or symptoms selected and an associate list of test procedures to be performed to check for those causes. The test procedures are listed in the order of the probability or likelihood that the test will be successful in diagnosing the cause of the selected symptom or symptoms. In one embodiment, the diagnostic system 10 presents a list of suggested fixes for each symptoms such that the user may proceed to repair the vehicle directly.

Once the symptom or symptoms have been selected and the associated recommended test procedures displayed, the user can select one of the displayed test procedures, and the system will then launch or initiate that procedure. While the screen display 39 lists a recommended order for performing listed tests, the user is free to perform the tests in any order desired.

Once the user selects the test to be performed, the diagnostic system 10 queries a test library database coupled to the diagnostic system 10 to determine what support modules, sensors, and/or circuits are needed for the particular test to be performed. The diagnostic system 10 may provide prompts instructing the user connect the needed support modules, sensors, and/or circuits to the vehicle and the diagnostic system 10. For example, the user will be instructed in the manner of connecting and using a scanner for downloading information from the vehicle on-board computer and/or controlling operation of certain computer functions.

The diagnostic system 10 provides a feedback mechanism for users to provide data related to effective diagnostic results to the expert service system 50. The diagnostic system 10 may provide a "Confirm Diagnosis" icon on the screen. After the user performed a selected test procedure and found the root cause for the selected symptom or symptoms, the user may click the Confirm Diagnosis icon to indicate that the selected test procedure is an effective test for the selected symptom or symptoms. In response, the diagnostic system 10 stores data related to the effective test and the corresponding symptom or symptoms, including the vehicle model under diagnosis, the symptoms, the test name, etc.

The diagnostic system may maintain a database to manage the data related to the effective test and corresponding symptoms. The diagnostic system 10 tracks the number of each effective test corresponding to each symptom. Whenever the user indicates an effective test effectively isolates the cause of a symptom or fault, the diagnostic system 10 may increment the count for the test. The database may reside in the storage device 210 of the data processing system 100, and/or in a remote data processing system connecting to the diagnostic system 10 via a data transmission network. In one embodiment, the diagnostic system 10 sends the data related to the effective test to the expert service system 50 after each diagnosis.

If a test other than the recommended tests found the cause of the symptom or fault, the diagnostic system 10 may present a text box for the user to enter a brief description of the test used to isolate the cause of the symptoms. That data is also saved in a manner as described relative to the effective tests.

Figure 3:
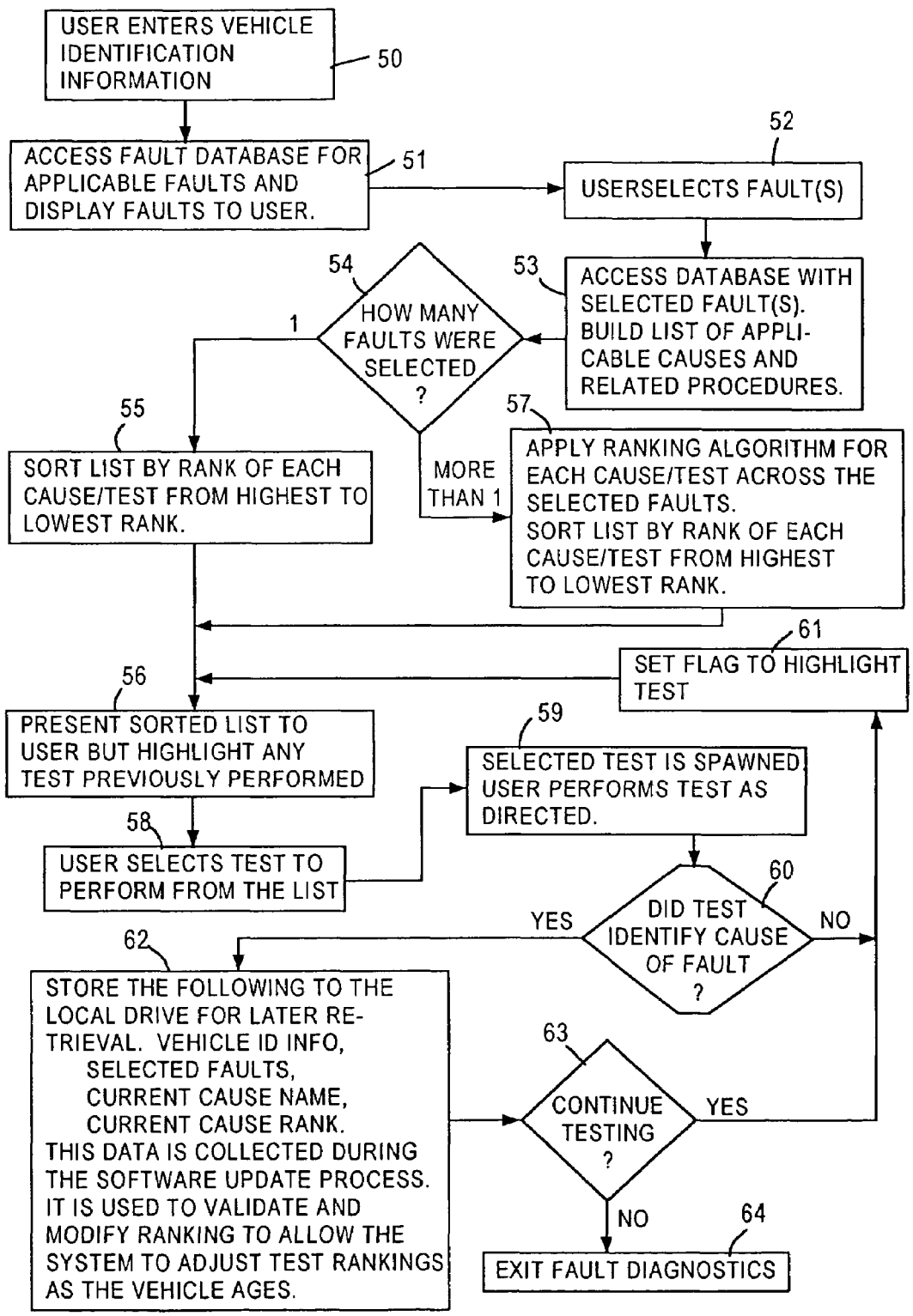
FIG. 3 is a flow chart illustrating the operation steps of the diagnostic system.

FIG 3 is a flow chart illustrating the operation of the diagnostic system 10. In step 50, the user enters vehicle identification information and selects the Test/Analysis icon, which brings up a screen as shown in FIG 3. In Step 51, the diagnostic system 10 accesses the appropriate database and displays a list of faults corresponding to the vehicle under diagnosis to the user as shown in FIG 3. The user then selects one or more faults (Step 52). In response, the diagnostic system 10 accesses the database with the selected faults, and retrieves information related to applicable causes and related test procedures (step 53). If only one fault is selected, the diagnostic system 10 sorts the list of possible causes by their respective ranks and presents the list to the user along with tests which have been previously performed (Step 56). If more than one fault was selected, the diagnostic system 10 applies a ranking algorithm for each cause/test and presents the list of possible cause/test to the user (Steps 56 and 57). In Steps 58, the user selects a test to be performed. In response, the diagnostic system 10 performs the selected test process (Step 59). In step 60, the user indicates, using an appropriate icon, whether the test identified the cause of the fault. If the selected test effectively isolates the cause of the symptom or symptoms, the diagnostic system 10 stores data related to the effective test in a database (Step 62). The user is then prompted whether testing should continue (Step 63). If so, the last test performed is again highlighted (Step 61); if not, the diagnostic system 10 exits the fault testing mode (Step 64).

The diagnostic system 10 may collection additional information related to diagnostics conducted by the diagnostic system 10. For example, information related to ineffective tests/fixes corresponding to various symptoms/faults can be collected. Information related to the technician who conducted the diagnostics can also be collected by the diagnostic system 10. For example, the diagnostic system 10 may request a technician to input his or her experience range, such as experienced, inexperienced, etc.

Machine-readable instructions implementing the above-described process may be stored in, and executed by, the diagnostic system 10. The machine-readable instructions may be stored in a machine-readable storage medium, such as optical disks, hard disks, tapes, electronic waves, etc., and distributed to customers. The machine-readable instructions may also be distributed via the Internet. Customers who wish to have their diagnostic systems to perform the above-mentioned process may download the instructions from the expert service system 50 and/or a web site, and install the programs on their own systems.

Collection and Processing of Diagnostic Results

As discussed earlier, for every diagnostic process, the diagnostic system 10 stores data related to effective diagnostic results in a data storage device of the diagnostic system 10 or in a remote data processing system coupled to the diagnostic system 10 via a data transmission network. The diagnostic results may include attributes of the vehicles (year, make, model, engine particulars, etc.), symptoms or faults, effective tests for finding causes of a specific symptom, effective fixes corresponding to a specific fault, measurements obtained during the diagnoses, information obtained from vehicle on-board computers, additional comments/descriptions entered by technicians, ineffective tests/fixes corresponding to various symptoms/faults, information related to the technician who conducted the diagnostics can also be collected by the diagnostic system, etc. The expert service system 50 and the diagnostic systems 10 use a predetermined protocol to allow the expert system 50 to access the data related to diagnostic results.

According to one embodiment, the saved data is retrieved when the diagnostic system 10 connects to the expert service system 50 via the data transmission network 52. The diagnostic system 10 may connect to the expert service system 50 for various reasons. For example, the diagnostic system 10 may connect to the expert service system 50 to download updated software for providing expert diagnostic suggestions as described earlier relative to FIGS. 2 and 3. The diagnostic system 10 may be required to connect to the expert service system 50 whenever the diagnostic system 10 is operating to access the most updated software stored in the expert service system 50 to perform expert diagnostic services. According to another embodiment, the data collected by the diagnostic systems 10 may be sent to the expert service system 10 via means other than direct data communications. For example, the data can be sent to the expert service system 10 via mail or telephone.

Figure 4:
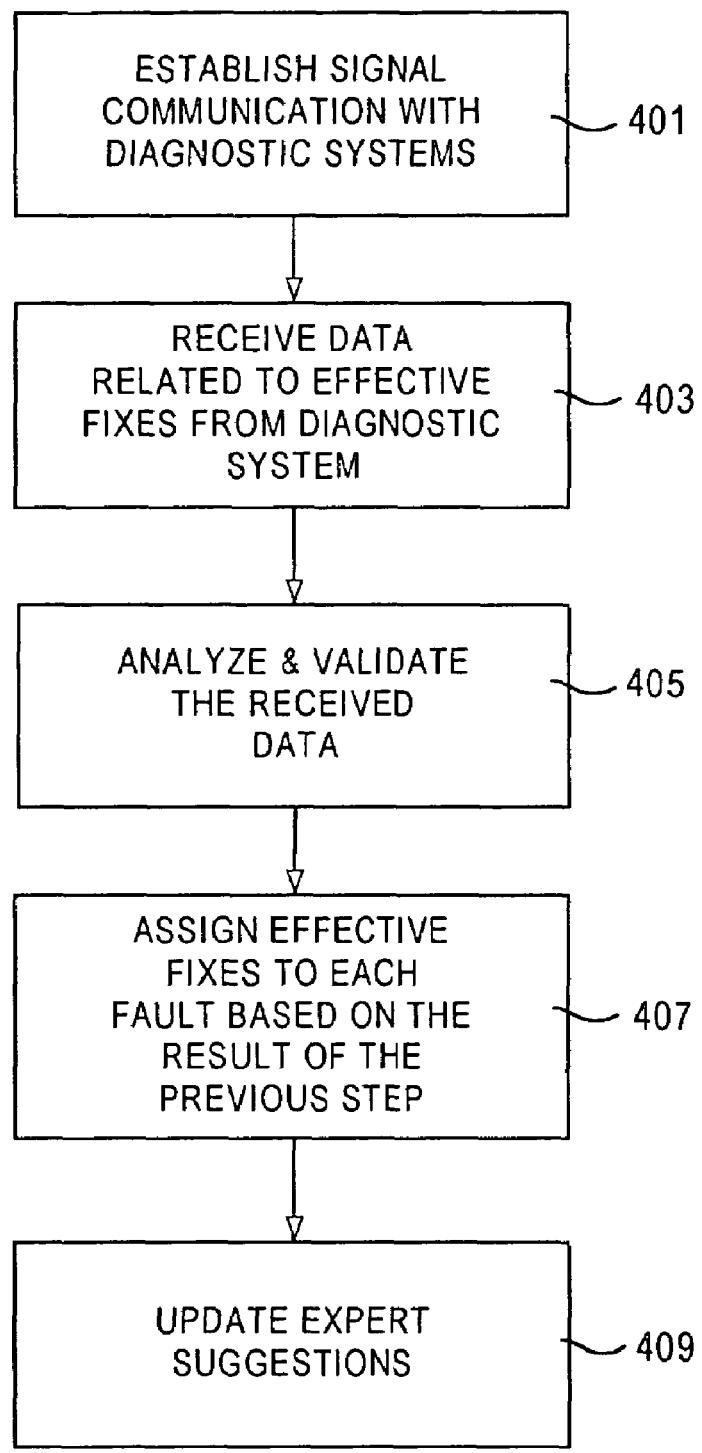
FIG. 4 is a flow chart showing the operation of the expert service system.

Referring to FIG. 4, after the diagnostic system 10 is connected the expert service system 50 (Step 401), the expert service system 50 may generate a request signal to the diagnostic system 10 to request data related to the diagnostic results. In response to the request signal, the diagnostic system 10 accesses the data related to the diagnostic results and send it to the expert service system 50 (Step 403). After the data has been sent to the expert service system 50, the diagnostic system may set flags to indicate that the data has be sent. Alternatively, the diagnostic system 10 may delete the data from the data storage device in which the data is stored.

According to another embodiment, after the diagnostic system 10 is connected to the expert service system 50 via the data transmission network 52, the diagnostic system 10 periodically gathers the data related to effective diagnostic results and sends it to the expert service system 50. Alternatively, the expert service system 50 may periodically issues a request signal to request the diagnostic system 10 to send the data related to effective diagnostic results to the expert service system 50.

The expert service system 50 maintains a database to manage the data related to effective diagnostic results received from the diagnostic systems 10. After the data arrives from the diagnostic systems 10, the expert service system 50 may sort the data based on the symptoms or faults addressed and their corresponding fixes and/or tests (Step 405). The expert service system 50 tracks the number of each effective fix or test corresponding to each symptom or fault. For each symptom or fault, the expert service system 50 ranks the effective fixes or tests corresponding to the symptom or fault based on their respective numbers. In Step 407, the expert service system 50 assigns only top ranked fixes or tests to each fault or symptom as effective fixes or tests, and updates the software for providing expert diagnostic suggestions accordingly (Step 409). For example, the expert service system 50 may assign top 10 tests or fixes corresponding to each fault or symptom as their respective effective tests or fixes.

Alternatively, the expert service system 50 may calculate an index for each fix or test corresponding to each symptom or fault based on, for example, the number of times each fix/test fixed/diagnosed each symptom/fault for each specific vehicle, or the ratio of the number of times each fix/test successfully fixed/diagnosed each symptom/fault for each specific vehicle, to the number of times the fix/test used to fix/diagnose the symptom/fault. The expert service system 50 may use any type of indices that is indicative the effectiveness of each fix/test. The expert service system 50 then updates the recommendations stored in the database based on the ranking of the index.

The expert service system 50 may perform additional analysis to screen the data received from the diagnostic systems 10. After data related to effective diagnostic results is received, the expert service system 10 performs a validation process to determine whether the fixes or tests corresponding to each symptom or fault are effective. The data may be reviewed by a group of experts who will indicate whether a specific test or fix corresponding to the fault or symptom is valid. The level of experience of a technician who conducted the diagnosis may be taken into consideration during the validation process. A validation result is input to the expert service system 50. Only valid fixes or tests can be assigned as effective fixes or tests by the expert service system 50.

As discussed earlier, the diagnostic systems 10 allow users to submit information related to effective tests or fixes other than the recommended tests/fixes corresponding to specific symptoms or faults. The diagnostic system 10 may present a text box for the user to enter a brief description of the test used to isolate the cause of the symptoms. That data is also saved in the diagnostic system 10 and accessible by the expert service system 50. The expert service system 50 apply a validation process similar to that discussed above to validate the fixes/tests, and add the fixes/tests to the expert suggestions based on the validation result.

According to another embodiment, the expert service system 50 performs additional analysis on the data received from the diagnostic systems to provide a prediction of possible failure of a specific part and/or component for a specific model year of vehicle. For each vehicle of a specific model year, the expert service system 50 may use statistical methods, such as regression analysis, to determine what components may experience problem after a certain mileage range or period of time based on the data received from the diagnostic systems. For example, based on data related to numerous diagnostic results related to Honda Accord, the expert service system 50 may determine that the vehicle's timing belt is likely to experience a failure after 80,000 miles or five years after purchase. The result is included in the expert suggestions. Once the diagnostic system 10 receives such data, the diagnostic system may generate a report to vehicle owners regarding possible failures of various components so that preventative measure can be taken to prevent unexpected breakdown. The diagnostic systems 10 may link the data related to expert suggestions to a client database that includes data related to client's vehicles and personal information, such as name, telephone number and address. When the client's vehicle fits the prediction scenario, such as after certain mileage, the diagnostic system 10 may prompt technicians to notify the vehicle owner for a check.

After the software for providing expert suggestions is updated, the expert service system 50 allows the diagnostic systems 10 to download the updated software to provide expert diagnostic suggestions using the updated suggested list of tests or fixes reflecting the newest update of the expert suggestions. The diagnostic systems 10 may issue a request signal to the expert service system 50 to access the most updated expert diagnostic suggestions. In response, the expert service system 50 controls the software including the most updated expert diagnostic suggestions to be delivered to the diagnostic systems that requested access to the software. The software implementing the expert suggestions may also be distributed to customers via CD-ROMs, cartridges, add-on cards, the internet, etc.

System Security and Management

The expert service system 50 may allow only authorized diagnostic systems to access or receive information related to updated expert diagnostic suggestions. Each diagnostic system 10 may be assigned a unique identification code, which is sent to the expert service system 50 when the diagnostic system 10 establishes communication with the expert service system 50. The expert service system 50 maintains a list of authorized diagnostic systems, such as diagnostic systems that had sent data related to effective diagnostic results to the expert service system 50 or had paid or subscribed to sue the service, or diagnostic systems that were purchased from a specific source.

The expert service system 50 may be implemented as a server allowing diagnostic systems 10 to connect to the server via the internet, intranet, and/or LAN, and the like. In order to limit access to valid users only, the expert service system 50 controls the distribution of updated expert suggestions based on, for example, a product code unique to each diagnostic system made by a specific company. Every diagnostic system 10 sold by the specific company includes a circuit or add-on card with an embedded product code unique to each machine. Alternatively, the product code may be generated by a software application and stored in a specific location of non-volatile memories that is accessible by software applications.

The expert service system 50 maintains a database for valid product codes, such as product codes for all diagnostic systems made by the specific company. Each time a diagnostic system 10 connects to the expert service system 50 to access data related to updated expert suggestions, the expert service system 50 will require submission of the product code. The product code can be submitted by manual entry or automatic retrieval by software running on the diagnostic system.

Based on the product code submitted by the diagnostic system, the expert service system 50 accesses the user database of valid product codes and determines whether the received product code matches one of the valid product codes. In response to a match, the expert service system 50 authorizes the diagnostic system 10 to access the data; otherwise, access is denied.

According to one embodiment, system security may be obtained by using activation codes to control distribution of the data related to expert suggestions. An activation code is similar to a key to unlock the service data downloaded to diagnostic systems. Only authorized users will be provided with an activation code. Without a valid activation code, even if data related to expert suggestions is properly downloaded, it cannot be properly installed on or used by the diagnostic system. The activation code may be provided to customers when the diagnostic systems 10 are shipped, or may be obtained by telephone or e-mail when users subscribe to the service.

Activation codes can be used in conjunction with product codes to achieve higher system security. For instance, the expert service system 50 generates an activation code based on a product code submitted by a valid user. The activation code is then sent to the user for activating the downloaded data. A software program that runs on the diagnostic system will access the product code of the diagnostic system and determine whether the product code of the diagnostic system matches with the product code from which the activation code is generated. Unless a proper match is obtained, the activation code will not unlock the downloaded software. By this process, verification of identities of hardware and software is conducted. Thus, duplicates of downloaded service data and activation code cannot properly operate on other unauthorized diagnostic systems, as a check of product codes would not generate a match.

The expert service system 50 may also control access to the system by creating a database for valid users. For example, only those users paying fees can access to the data related to updated expert suggestions. Users will be requested to log in every time with a user ID and password so that the expert service system 50 may determine identity of a user. Automatic log-in can be achieved by verifying identity codes embedded in the requests sent by a diagnostic system. For example, when a user uses a web browser to access the website maintained by the expert service system 50, "cookies," which are widely used to track a specific computer system, can be utilized to determine a user's identity and whether the system has subscribed to the service.

The expert service system 50 may allow users to purchase a license to download data related to updated expert suggestions. The license allows a user to access the data related to updated expert suggestions for a certain period of time. A license code will be generated and sent to the licensee. In certain aspects, a license code is similar to an activation code described above, as the license code is necessary for unlocking and accessing the downloaded data related to updated expert suggestions. The license code may be stored at a specific location on a non-volatile memory. The downloaded data related to updated expert suggestions, when executed or accessed, will verify whether a valid license code exists.

In order to ensure that the downloaded data is effective only within the licensed period, an expiration date is encoded into the license code. When the diagnostic system executes or accesses the downloaded service data, the license code will be read out and compared with system time to determine whether the license is still valid.

Other information can also be embedded in the license code to increase system security. The expert service system 50 may allow a diagnostic system 10 to access the service data even if the diagnostic system is without a unique product code. The diagnostic system 10 will be asked to download an installation program. The installation program, when executed, accesses the controller of a hard disk installed on the diagnostic system and obtains a serial number of the hard disk. The installation program then generates a unique ID based on the serial number of the hard disk. The unique ID is treated as a product code as described above and sent to the expert service system 50. After the user is properly licensed, the unique ID is used to generate an activation code or license code as discussed above.

The expert diagnostic service and system described above may be utilized with any appropriate diagnostic systems, such as medical diagnostic systems for diagnosing patients, battery testers for testing batteries, engine analyzer for analyzing engines, and the like.

The disclosure has been described with reference to specific embodiments thereof. It will, however, be evident that various modifications and changes may be made thereto without departing from the broader spirit and scope of the disclosure. The concepts described in the disclosure can apply to various operations of the networked presentation system without departing from the concepts. The specification and drawings are, accordingly, to be regarded in an illustrative rather than a restrictive sense.

What is claimed is:

1. An expert diagnostic service method comprising the steps of:
   collecting data related to fixes corresponding to various symptoms from a plurality of diagnostic systems via a data transmission network;
   accessing a validation result of validated fixes corresponding to each of the various symptoms, wherein the validation result is generated by performing a validation process to screen out invalid fixes from the collected data; and
   assigning at least one effective fix to one of the various symptoms based on an accumulated number of each of the validated fixes corresponding to the one of the various symptoms.

2. The method of claim 1, further generating data including the at least one effective fix assigned to the one of the various symptoms.

3. The method of claim 2 further comprising the steps of:
   receiving a request to access to the data including the at least one effective fix assigned to the one of the various symptoms from one of the plurality of diagnostic systems via the data transmission network;
   transmitting the data including the at least one effective fix assigned to the one of the various symptoms to the one of the plurality of diagnostic systems via the data transmission network; and
   receiving data related to effective fixes corresponding to various symptoms from the one of the plurality of diagnostic systems via the data transmission network.

4. The method of claim 1 further rendering a result of the assigning step available to at least one of the plurality of diagnostic systems.

5. The method of claim 1, wherein the plurality of diagnostic systems are selected from the group consisting of an engine analyzer, an aligner, a balancer, and a battery tester.

6. The method of claim 1, wherein the data related to fixes results includes at least one of attributes related to an apparatus under diagnosis, a cause of a fault, a test for finding a cause of a fault, and a fix to cure a cause of a fault.

7. An expert diagnostic method comprising the steps of:
collecting data related to diagnostic results corresponding to various faults from a plurality of diagnostic systems via a data transmission network;
accessing a validation result of validated diagnostic results corresponding to each of the various symptoms, wherein the validation result is generated by performing a validation process to screen out invalid diagnostic results from the collected data; and
assigning at least one effective diagnostic result to one of the various symptoms based on an accumulated number of each of the validated effective results corresponding to the one of the various symptoms;
wherein the data related to diagnostic results includes at least one of a test for finding a cause of a fault and a fix to cure a cause of a fault.

8. The method of claim 7 further generating data including the at least one effective diagnostic result assigned to the one of the various symptoms.

9. The method of claim 8 further comprising the steps of:
receiving a request to access to the data including the at least one effective diagnostic result assigned to the one of the various symptoms from one of the plurality of diagnostic systems via the data transmission network;
transmitting the data including the at least one effective diagnostic result assigned to the one of the various symptoms to the one of the plurality of diagnostic systems via the data transmission network; and
receiving data related to diagnostic results corresponding to various symptoms from the one of the plurality of diagnostic systems via the data transmission network.

10. The method of claim 7, further rendering a result of the assigning step available to at least one of the plurality of diagnostic systems.

11. The method of claim 7, wherein the diagnostic systems are configured to diagnose a vehicle or a patient.

12. A data processing system for providing expert diagnostic services comprising:
a data processor for processing data;
a data communication port for connecting to a data transmission network;
a data storage device for storing instructions; and
a data transmission path coupled to the data processor, the data communication port, and the data storage device;
wherein the instructions, when executed by the data processor, control the data processing system to perform the machine-implemented steps of:
receiving data related to diagnostic results corresponding to various symptoms from a plurality of diagnostic systems via the data transmission network;
accessing a validation result of validated diagnostic results corresponding to each of the various symptoms, wherein the validation result is generated by performing a validation process to screen out invalid diagnostic results from the collected data; and
assigning at least one effective diagnostic result to one of the various symptoms based on an accumulated number of each of the validated diagnostic results corresponding to the one of the various symptoms;
wherein the data related to diagnostic results includes at least one of a test for finding a cause of a fault and a fix to cure a cause of a fault.

13. The system of claim 12, the storage device further stores instructions, when executed by the data processor, control the data processing system to generate data including the at least one effective diagnostic result assigned to the one of the various symptoms.

14. The system of claim 13, wherein the storage device further stores instructions that, when executed by the data processor, control the data processing system to perform the machine-implemented steps of:
receiving a request to access to the data including the at least one effective diagnostic result assigned to the one of the various symptoms from one of the plurality of diagnostic systems via the data transmission network;
transmitting the data including the at least one effective diagnostic result assigned to the one of the various symptoms to the one of the plurality of diagnostic systems via the data transmission network; and
receiving data related to diagnostic results corresponding to various symptoms from the one of the plurality of diagnostic systems via the data transmission network.

15. The system of claim 12, wherein the storage device further stores instructions that, when executed by the data processor, control the data processing system to render a result of the assigning step available to at least one of the plurality of diagnostic systems.

16. The system of claim 12, wherein the diagnostic systems are configured to diagnose a vehicle or a patient.

17. A machine-readable medium bearing instructions for providing expert diagnostic services, the instructions upon execution by a data processing system causing the data processing system to perform the steps of:
receiving data related to diagnostic results corresponding to various faults from a plurality of diagnostic systems via the data transmission network;
accessing a validation result of validated diagnostic results corresponding to each of the various symptoms, wherein the validation result is generated by performing a validation process to screen out invalid diagnostic results from the collected data; and
assigning at least one effective diagnostic result to one of the various symptoms based on an accumulated number of each of the validated diagnostic results corresponding to the one of the various symptoms;
wherein the data related to diagnostic results includes at least one of a test for finding a cause of a fault and a fix to cure a cause of a fault.

18. The medium of claim 17 further bearing instructions upon execution by a data processing system causing the data processing system to generate data including the at least one effective diagnostic result assigned to the one of the various symptoms.

19. The medium of claim 18 further bearing instructions that, upon execution by a data processing system, cause the data processing system to perform the machine-implemented steps of:
receiving a request to access to the data including the at least one effective diagnostic result assigned to the one of the various symptoms from one of the plurality of diagnostic systems via the data transmission network;
transmitting the data including the at least one effective diagnostic result assigned to the one of the various symptoms to the one of the plurality of diagnostic systems via the data transmission network; and receiving data related to effective diagnostic results corresponding to various symptoms from the one of the plurality of diagnostic systems via the data transmission network.

20. The medium of claim 17, further bearing instructions that, upon execution by a data processing system, cause the data processing system to render a result of the assigning step available to at least one of the plurality of diagnostic systems.

21. The medium of claim 17, wherein the diagnostic systems are configured to diagnose a vehicle or a patient.

22. An expert diagnostic service method comprising the steps of:
 collecting data related to fixes corresponding to various symptoms from a plurality of diagnostic systems via a data transmission network;
 accessing a validation result of validated fixes corresponding to each of the various symptoms, wherein the validation result is generated by performing a validation process to screen out invalid fixes from the collected data;
 generating an index for each of the validated fixes corresponding to each of the various symptoms based on an accumulated number of each of the validated fixes corresponding to each of the various symptoms; and
 assigning at least one effective fix to one of the various symptoms based on the index for each of the validated fixes corresponding to the one of the various symptoms.

* * * * *